United States Patent [19]

Andresen et al.

[11] Patent Number: 4,867,947
[45] Date of Patent: Sep. 19, 1989

[54] INTERFACE FOR LIQUID CHROMATOGRAPH-MASS SPECTROMETER

[75] Inventors: Brian D. Andresen, Pleasanton; Eric R. Fought, Livermore, both of Calif.

[73] Assignee: Sepragen Corporation, San Leandro, Calif.

[21] Appl. No.: 904,953

[22] Filed: Sep. 8, 1986

[51] Int. Cl.⁴ ................. H01J 49/26; G01N 30/72
[52] U.S. Cl. ......................... 422/70; 250/289; 250/288; 422/78; 436/149; 436/161
[58] Field of Search ............... 422/70, 66; 436/161, 436/44; 73/61.1 C; 250/289, 288 A; 141/367; 198/840

[56] References Cited

U.S. PATENT DOCUMENTS

| 1,290,894 | 2/1987 | Bryan | 198/840 |
| 2,410,611 | 11/1946 | Pratt et al. | 198/840 |
| 2,847,114 | 8/1958 | Orr | 198/840 |
| 4,055,987 | 11/1977 | McFadden | 250/288 A |
| 4,178,507 | 12/1979 | Brunne et al. | 250/288 A |
| 4,594,506 | 6/1986 | Ghaderie | 250/288 A |

FOREIGN PATENT DOCUMENTS 152747 8/1985 European Pat. Off. ........ 250/288 A

OTHER PUBLICATIONS

Smith et al., *Anal. Chem;* No. 53, (1981), pp. 1603–1611.
Hayes et al., Anal. Chem., No. 55, (1983), pp. 1745–1752.

Primary Examiner—Michael S. Marcus
Attorney, Agent, or Firm—Shyamala T. Rajender

[57] ABSTRACT

A moving belt interface for real-time, high-performance liquid chromatograph (HPLC)/mass spectrometer (MS) analysis which strips away the HPLC solvent as it emerges from the end of the HPLC column and leaves a residue suitable for mass-spectral analysis. The interface includes a portable, stand-alone apparatus having a plural stage vacuum station, a continuous ribbon or belt, a drive train magnetically coupled to an external drive motor, a calibrated HPLC delivery system, a heated probe tip and means located adjacent the probe tip for direct ionization of the residue on the belt. The interface is also capable of being readily adapted to fit any mass spectrometer.

22 Claims, 4 Drawing Sheets

INTERFACE FOR LIQUID CHROMATOGRAPH-MASS SPECTROMETER

The invention described herein arose in the course of, or under Contract No. W-7405-ENG-48 between the U.S. Department of Energy and the University of California for the operation of the Lawrence Livermore National Laboratory.

This invention relates to an interface between a high performance liquid chromatograph (HPLC) column and a mass spectrometer (MS), particularly to a moving belt type interface, and more particularly to an improved moving belt interface for real-time HPLC-MS analysis, particularly adapted for polar compounds.

BACKGROUND OF THE INVENTION

Mass spectrometry works very well for the analysis of most substances. The technique produces very specific data and is very sensitive. However, for the analysis of very polar compounds or high molecular weight substances, mass spectral analyses require special procedures. Probe distillation of pure compounds is the method most often selected. But, probe distillation of pure compounds can only be used if the substance to be analyzed can, at some temperature below its thermal degradation point, be sublimed into the ion source of the mass spectrometer.

In order to circumvent the problems associated with the heating of very polar compounds which can easily decompose with heat, other ionization techniques have been devised for mass spectral analysis. These include field desorption, field ionization, surface ionization and fast atom bombardment. These techniques are usually applied to relatively pure substances and are seldom used for the real-time analysis of polar compounds in complex mixtures. Therefore, a method was needed which would allow first, for the separation of polar compounds and secondly, for the delivery of relatively pure substances into the ion source of the mass spectrometer.

Analytical methods currently employed in many laboratories require samples to be first analyzed by HPLC in one laboratory and then hand carried to the mass spectrometry facility for further analysis. This requires time and additional sample preparation.

However, methods are currently available which allow effluents from high performance liquid chromatography columns to be carried directly into the ion source of the mass spectrometer. These methods can be highlighted into four general groups. Each has its own advantages and associated problems.

1. Direct Introduction: This technique relies on a powerful vacuum pumping system which allows the HPLC effluent to flow directly into the ion source of the mass spectrometer. Very significant increases in vacuum pressure, which is one of the major drawbacks in this technique, are controllable, if only a very small sample of the effluent is presented (split) from the bulk of the HPLC effluent. The direct introduction of HPLC effluent into the ion source does not allow for high resolution mass spectral analyses, which requires very low pressures in the analyzer section and a very stable vacuum. Fluctuations in the vacuum pressure affect the results significantly. Only volatile HPLC solvents can be used with this technique. Additionally, the method is less sensitive because a major portion of the sample is not analyzed. Only chemical ionization appears to be susceptible to analysis by this technique.

2. Thermospray: This technique has become very popular and relies on the rapid evaporation of the HPLC solvent as it passes through a heated capillary tube. A supersonic jet of vapor containing the compounds to be analyzed is allowed to pass adjacent to a draw-out plate which directs ionized compounds directly into the analyzer section of the mass spectrometer. This technique requires the HPLC solvent to be volatile. More significant is the requirement that the ion source of the mass spectrometer needs to be replaced or significantly modified. Thermospraying is not applicable to high resolution mass spectral analysis.

3. Atmospheric Pressure Mass Spectrometry: This technique relies on the use of a nebulizer which mixes the HPLC effluent with a high pressure stream of nitrogen gas. The vaporized HPLC solvent is then allowed to pass through a corona discharge and into the analyzer section of the mass spectrometer. This is a dedicated detector for the HPLC-mass spectrometer. This technique appears to work well for only for more volatile compounds and the best information is obtained only with special (triple quadrupole) analyzer instruments.

4. Membrane Separator: This technique relies on the selective migration of compounds through a porous membrane. The membrane is placed in front of the ion source and the effluent of the HPLC column is allowed to pass over this porous material. This type of HPLC-MS interface allows substantial amounts of the HPLC solvent into the mass spectrometer. The temperature of the mass spectrometer, flow rates and type of membrane material can greatly affect the migration of the compounds through the porous probe tip and thus significantly affect the resolution and sensitivity of the analyses.

5. Moving Belt Interface: This technique relies on the deposition of the HPLC solvent containing the sample to be analyzed, onto a moving wire or ribbon. The HPLC solvent is allowed to evaporate (by vacuum pumping and/or heating) directly off the moving belt as it is deposited thereon as the belt passes under the exit port of the HPLC column. The sample residue from the evaporation step is then carried directly into the ion source of the mass spectrometer. As the moving belt enters the ion source, chemicals are either vaporized off the surface of the belt by the application of external heat or ionized directly on the surface by bombardment with an electron beam. The integrity of the vacuum of the mass spectrometer is maintained substantially undisturbed, because the HPLC solvents are removed a considerable distance from the ion source and thus do not enter the ion source.

The moving belt interface is more amenable to high resolution mass spectral analysis. The ion source, analyzer section and the vacuum pumping section of the mass spectrometer do not necessarily need to be significantly altered or replaced, although commercially available interfaces seem to require that the interface must be permanently bolted to the normal solid probe inlet system of the mass spectrometer. However, the prior art moving belt interface has its own drawbacks. Because of the time delay between the deposition of the sample on the moving belt and analysis as the belt moves into the ion source of the mass spectrometer (20-30 seconds), volatile compounds can be lost in the vacuum system of the interface. As with the other techniques herein described, the moving belt interface can not handle HPLC solvents which contain nonvolatile buffer components. The mode and timing of the introduction of the HPLC effluent into the HPLC-MS interface is most critical. An uneven application can result in an overlap of compounds which were completely resolved by the HPLC column.

Various types of approaches to improving moving belt interfaces have been previously considered. These prior art approaches are exemplified by the following publications and patents:

1. "Deposition Method For Moving Ribbon Liquid Chromatograph-Mass Spectrometer Interfaces", R. D. Smith et al., Anal. Chem., 53, 739-740 (1981);

2. "Liquid Chromatography-Mass Spectrometry with Electron Impact And Fast Ion Bombardment with A Ribbon Storage Interface", R. D. Smith et al., Anal. Chem., 53, 1603-1611 (1981);

3. "Moving Belt Interface with Spray Deposition For Liquid Chromatography/Mass Spectrometry", M. J. Hayes et al., Anal. Chem., 55, 1745-1752 (1983);

4. "A Comparison Of Moving Belt Interfaces For Liquid Chromatography-Mass Spectrometry", D. C. Games, et al., Biomedical Mass Spectrometry, 11(2), 87-95 (1984);

5. "Simplified Moving Belt Interface For Liquid Chromatography/Mass Spectrometry", S. D. Stout et al., Anal. Chem., 57, 1783-1786 (1985);

6. "Method For The Analysis Of Materials By Chromatography And Mass Spectrometry", U.S. Pat. No. 4,501,817 issued Feb. 26, 1985, to Brian D. Andresen and Kwokei J. Ng;

7. "Liquid Chromatograph/Mass Spectrometer Interface", U.S. Pat. No. 4,160,161 issued July 3, 1979 to Robert L. Horton;

8. "Interface For Use In A Combined Liquid Chromatography-Mass Spectrometry System", U.S. Pat. No. 4,112,297 issued Sept. 5, 1978 to Hirayuki Miyogi et al;

9. "Liquid Cnromatograph/Mass Spectrometer Interface", U.S. Pat. No. 4,055,987 issued Nov. 1, 1977 to william H. McFadden, describes a liquid chromatograph/mass spectrometer interface which permits continuous introduction of dilute solutions into the ion source of a mass spectrometer. A ribbon loop and a drive therefor serve to receive the solution from the liquid chromatograph. The solution is then carried by the moving ribbon or belt into a vacuum chamber and then into the ion source of the mass spectrometer. A heater positioned at or near the position where the solution from the chromatographic solution is received on the moving ribbon and another one placed close or adjacent to the ion source vaporize the solution into the ionization chamber;

10. "Liquid Chromatography-Mass Spectrometry System And Method", U.S. Pat. No. 3,997,298 issued Dec. 14, 1976 to Fred w. McLafferty et al;

11. "Method Of Coupling Thin Layer Cnromatograph with Mass Spectrometer", U.S. Pat. No. 3,896,661 Issued July 29, 1975 to Robert M. Parkhurst et al.

12. "Continuous-Flow Solution Concentrator And Liquid Chromatograph/Mass Spectrometer Interface And Methods For Using Both", U.S. Pat. No. 4,281,246 issued July 28, 1981 to V. Edward white et al describes an interface between a liquid chromatograph and mass spectrometer for conducting a liquid stream from the chromatographic column to the mass spectrometer. The stream passes continuously from the chromatographic column, heated along the way and fed into the ion source of the mass spectrometer; and 13. "Method And Apparatus For The Mass Spectrometric Analysis Of Solutions", U.S. Pat. No. 4,531,056 Issued July 23, 1985 to Michael J. Labowsky et al discloses an electrospray ion source for a mass spectrometer capable of generating ions, which are then pumped into the mass spectrometer through two vacuum chambers.

The major problems with the prior art liquid chromatography/mass spectrometry interfaces are (1) that each of the above mentioned methods for the analysis of HPLC effluent require either a new mass spectrometer which would accept the particular interface design, or (2) that the ion source, vacuum system and other components of the existing mass spectrometer require substantial modifications to accept and function with the interface, or (3) that the method is incapable of analyzing a wide variety of unique compounds which would be contained in the HPLC effluent. No one approach appears to be more desirable than the other and none of them provide a method or means for the direct, real-time analysis of polar compounds in HPLC effluents. Furthermore, these prior art devices are not stand-alone, portable units which can be used with any existing mass spectrometers, or units which are capable of handling the transition between the high pressures of HPLC columns to the near vacuum conditions of the mass spectrometer.

Therefore, a need exists to provide an interface which would allow chemical and biological compounds, particularly polar compounds, to be separated by liquid chromatography (LC), particularly, high performance liquid chromatography (HPLC) and sequentially or simultaneously analyzed by a mass spectrometer (MS). The interface must be capable of analyzing these compounds in real time, stripping away the LC or HPLC solvent as it emerges from the end of the column and leaving a residue suitable for mass spectral analysis. In addition, the interface must retain or maintain an adequate vacuum that is compatible with that in the mass spectrometer. A moving belt device which is capable of stripping away solvents from the LC or HPLC effluents must be provided. Compounds deposited on the belt should be capable of being vaporized or ionized off the surface of the belt (with a heater in the probe tip for example,) or ionized directly by fast atom or electron bombardment or by direct electron impact (surface ionization and such other techniques known in the art of mass spectrometry.

Therefore, it is an object of this invention to provide an improved moving belt interface for real-time LC or HPLC-MS analysis of chemical and biological compounds.

A further object of the invention is to provide an interface which allows polar compounds to be separated by conventional liquid chromatography or high performance liquid chromatography and sequentially or simultaneously analyzed by a mass spectrometer.

Another object of the invention is to provide an HPLC-MS interface which would strip away the LC or HPLC solvent as it emerges from the end of the LC or HPLC column and leave a residue suitable for mass spectral analysis.

Yet another object of the invention is to provide a moving belt interface for an HPLC-MS with a magnetically coupled drive train, a calibrated HPLC delivery system and a heated probe tip.

Another object of the invention is to provide such a moving belt interface which additionally includes a plurality of separate vacuum locks through which the moving belt passes, a portable stand-alone vacuum station, and means located adjacent the probe tip for ionization of the material on the moving belt.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention as embodied and broadly described herein, the present invention is directed to a real-time conventional LC or HPLC separation and MS analysis, in which a moving belt is utilized to carry the compounds eluted from the LC or HPLC column, such as for example, polar compounds, directly into the ion source of the mass spectrometer as they emerge from the tip of the LC or HPLC column. As used hereinafter, the term HPLC includes without limitation any conventional gravity flow or nigh pressure liquid chromatographic columns and effluents therefrom. Because mass spectrometers operate at very low pressures (of the order of $10^{-6}$ Torr) any evaporation of the HPLC solvent within or near the ion source of the mass spectrometer can contribute substantially to the background pressure which will substantially reduce the accuracy and efficiency of the performance of the mass spectrometer. The improved interface of the present invention provides solvent stripping chambers to reduce pressure overburdens on the mass spectrometer caused by evaporation of the HPLC solvent. The improved interface is light weight and easily transportable and adapted to b readily attachable to any mass spectrometer, without substantial or major modifications of the mass spectrometer. The interface includes a moving belt which is inert to the solvent, flexible, strong and amenable to the analyses of different types of chemical and biological compounds.

The moving belt interface of this invention is constructed so as to be utilized with existing mass spectrometers of various types and makes. Basically, the interface comprises differential pumping chambers, a magnetic drive mechanism, a durable ribbon or belt that is capable of withstanding high temperatures and corrosive solvents, preferably a stainless steel ribbon, for carrying compounds from the HPLC column into the ion source of the mass spectrometer, an externally heated probe tip to rapidly heat and evaporate the HPLC solvent off the moving belt and a magnetically positioned and controlled HPLC nozzle to precisely apply the HPLC effluent onto the moving belt as it passes under the nozzle. In addition, the moving belt is constructed to ensure that the moving belt would not slip off its "track", as it travels through the interface. A fast atom bombardment gun, for the direct ionization of the compound to be analyzed (analyte) on the moving belt, may be optionally included and located adjacent the heated probe tip. Additional detection of the HPLC effluent and read out means may also be optionally included and coupled adjacent the probe tip to provide for simultaneous read out of the HPLC and mass spectral data and analysis of the analyte during the operation of the interface.

BRIEF DESCRIPTION OF THE DRAWINGS

The accompanying drawings, which are incorporated herein and form a part of the specification, illustrate an embodiment of the invention and, together with the description, serve to explain the principles of the invention.

DETAILED DESCRIPTION OF THE INVENTION

Figure 1:
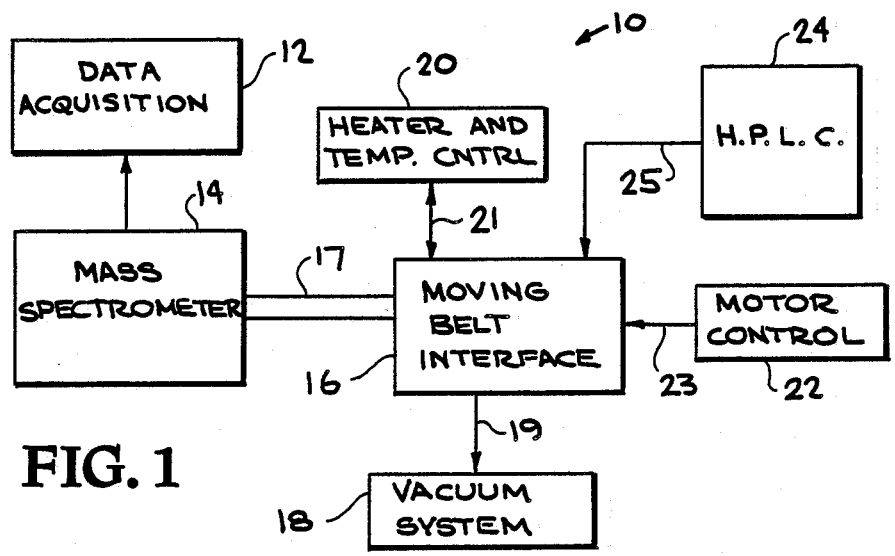
FIG. 1 is a block diagram of an overall system incorporating the moving belt interface of this invention.

The instant invention is directed to an improved moving belt interface between a high performance liquid chromatography (HPLC) column and a mass spectrometer (MS). The improved interface provides for real-time HPLC-MS analysis which strips away the HPLC solvent as it emerges from the end of the column, leaving on the moving belt a residue suitable for mass spectral analysis. The residue deposited on the moving belt can be vaporized off the surface thereof (to generate a thermospray) or ionized directly by fast atom bombardment into the ion source of the mass spectrometer. The interface of this invention allows polar compounds to be separated by HPLC and sequentially or simultaneously analyzed by a mass spectrometer, all at the same location.

The technique, utilizing the improved moving belt interface, generally comprises feeding materials, such as effluents from an HPLC column, onto a moving belt constructed out of any suitable flexible, inert material, preferably mylar, nylon or stainless steel, removing the HPLC solvent in separate vacuum locks or housing compartments so as to leave a chemical residue on the belt, and ionizing the residue by vaporization or by fast atom, electron or photon bombardment or by other ionization techniques known in the art, directly into the ion source of the mass spectrometer.

The apparatus for carrying out this technique includes a magnetically coupled, external drive mechanism for the moving belt, a mechanism for controlling the angle of the delivery of the HPLC effluent onto the moving belt, and a heated probe tip to rapidly heat and ionize or sublime off the chemical residue on the moving belt, while providing means for reducing the pressure at the point of effluent delivery (atmospheric pressure for example) to the vacuum conditions required of effective mass spectral analysis. As used herein, chemical residue means the residue left on the moving belt after evaporation of the HPLC solvent and includes, without limitation, organic, inorganic and/or biological materials. Optionally, a fast atom bombardment or electron gun for the direct ionization of the residue at the tip of the heated probe may be included. Additional detection and readout means may also be attached to the mass spectrometer adjacent the probe tip to monitor and/or analyze the operation of the interface.

An important aspect of the improved moving belt HPLC-MS interface of this invention is in the magnetically coupled mechanism for the belt device and for the control mechanism for HPLC effluent delivery onto the moving belt. These magnetically coupled approaches insure the maintenance of the integrity of the vacuum system of the mass spectrometer because no holes are required in the interface housing to accommodate the belt drive and effluent control and thereby avoid any leaks in the vacuum system.

The moving belt is preferably constructed of thin ribbons or belts of any suitable, inert and temperature resistant material such as some types of synthetic fibers, mylar or stainless steel. However, some plastic materials tend to stretch at elevated temperature or may be chemically reactive to HPLC solvents and/or the application of fast atom or electron bombardment.

The drive-train for the moving belt is o constructed to provide a smooth constant-force, non-slip drive. The non-slip surface of the belt power-drive and pulleys is provided by infusing a suitable plastic material onto the metal drives or pulleys over which the moving belt traverses. The main power-drive also includes an outwardly curved (convex) surface that continuously centers the belt. In addition, the drive-train includes a control which provides forward, reverse and variable speed stepper motor and drive for the moving belt.

The moving belt travels through a plurality of differentially pumped vacuum chambers (three in the illustrated embodiment). Each chamber is made vacuum tight except for two very small, off-set slits in the interconnecting walls or baffle plates through which the moving belt travels. The off-set or non-alignment of the slits from one chamber to the next is intended to aid in differential pumping without losing the vacuum to leaks in or between any of the chambers. The plural chamber vacuum housing may be provided with a glass window for observation, and of course, is constructed to be vacuum tight.

The angle of application or of directing the HPLC effluent onto the moving belt is critical for the uniform distribution of the sample solution on the belt, the uniform and quick evaporation of the HPLC solvent and for the formation of a thin, uniform layer of the sample residue on the surface of the moving belt. Therefore, the improved interface of this invention includes a calibrated HPLC delivery system, which includes a nozzle and slide mechanism which is magnetically coupled and remotely controlled. Thus, the position (angle) of the nozzle may be precisely controlled, while maintaining the integrity of the vacuum of the interface.

The improved interface includes a uniquely heated probe tip, which is inserted into the mass spectrometer, that can very rapidly heat up and sublime or ionize off the organic, inorganic or biological chemicals or molecules on the moving belt. This allows for no "belt memory" and for the chromatographic resolution of the HPLC effluent to be retained as the sample residue is fed or guided into the ion source of the mass spectrometer. Thus, better sensitivity for the analysis of the compounds deposited on the belt can be achieved.

A portable, plural stage, stand-alone vacuum station is utilized to pump the various chambers of the interface. A fast atom, or electron or photon bombardment gun may also be optionally utilized in conjunction with the improved interface for the direct ionization of chemicals on the moving belt.

The interface of this invention is portable and can be attached to any mass spectrometer without major modification of the spectrometer or its component parts. While the interface is particularly suited for separating polar or biological compounds by conventional HPLC techniques, and identifying and analyzing them substantially simultaneously or sequentially by a mass spectrometer, the interface is amenable to many types of experiments requiring the analysis of different classes of compounds.

Referring now to the drawings, FIG. 1 illustrates in block diagram form, a typical HPLC-MS system which incorporates the improved moving belt interface of the present invention. The illustrated system, generally indicated at 10, basically comprises a data acquisition computer or mechanism 12, which receives input from a mass spectrometer (MS) 14 as known in the art, MS 14 being connected to a moving belt interface 16 via a probe 17, the interface 16 being operationally connected to a vacuum pump system 18, as indicated by arrow 19, to a heater and temperature control 20, as indicated by double arrow 21, to a belt drive motor control 22, as indicated by arrow 23, and to a conventional HPLC column 24, as indicated by arrow 25. The operation of each of the components, the HPLC column 24, the mass spectrometer 14, and the data acquisition mechanism 12, is well known in the art, and these conventional components do not constitute part of the present invention. Thus, a detailed description of these components is deemed unnecessary. Moving belt interfaces and their function are also known in the art as exemplified by the publications and patents listed earlier, and thus their basic operation and function are not being described except when such description is necessary for or affects the construction and the operation of the improved interface of this invention illustrated in FIGS. 2–7.

Figure 2:
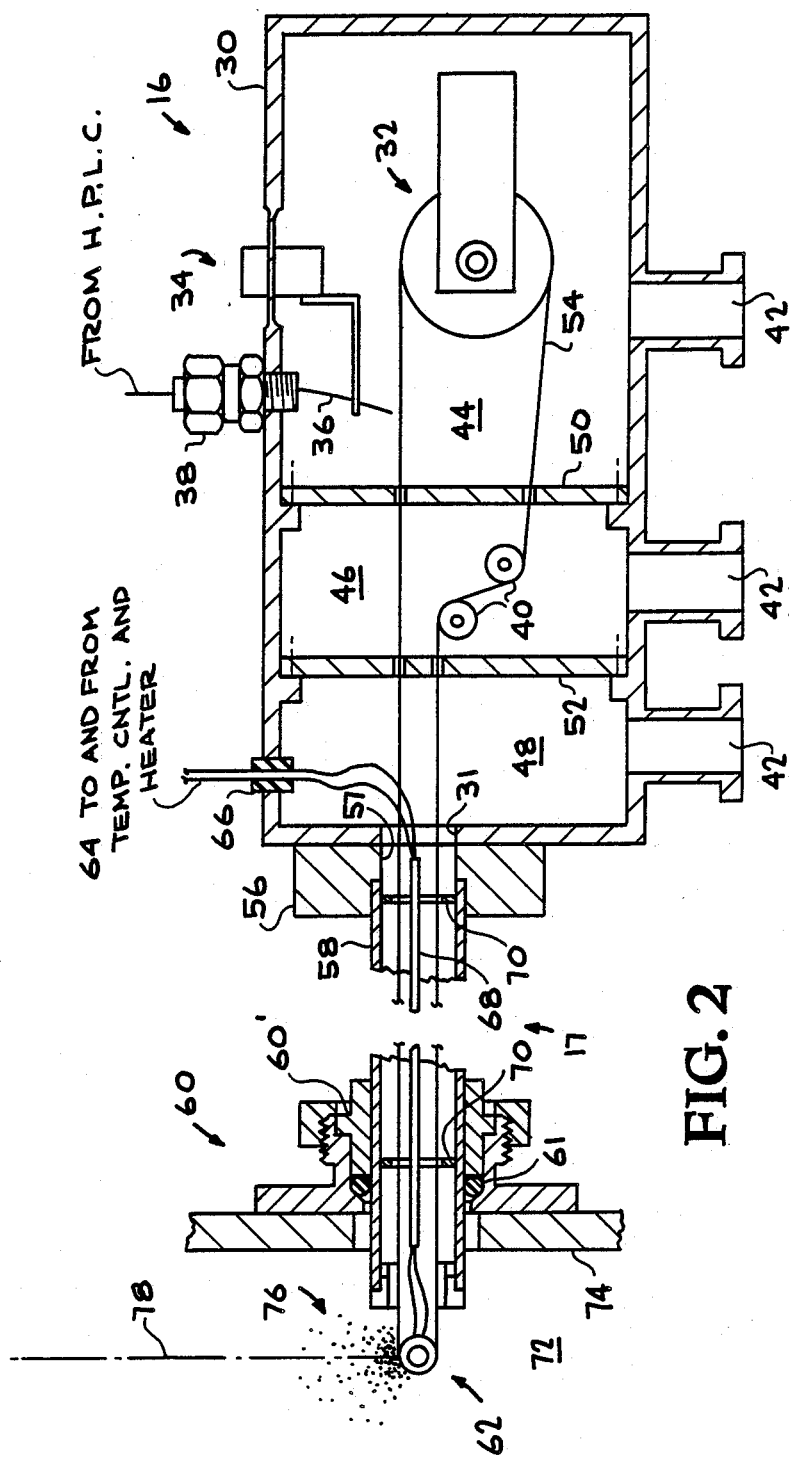
FIG. 2 is a cross-sectional view of an embodiment of an HPLC-MS interface made in accordance with the present invention.

The embodiment of the moving belt interface generally indicated at 16 as illustrated in FIG. 2, comprises a vacuum enclosure or housing 30 having three (3) chambers, in one of which is located a remote magnetic belt drive system, generally indicated at 32, a capillary or effluent tube positioning system, generally indicated at 34 for controlling the angle of a capillary or effluent tube 36 with respect to the moving belt, a capillary or effluent tube feed 38 which is adapted to be connected to an HPLC column, such as column 24 indicated in FIG. 1. Housing or enclosure 30 is constructed of any suitable material such as glass or quartz, acrylic, aluminum or stainless steel, for example, and provided with an opening 31 at one end thereof.

The vacuum pumping system 18 (see FIG. 1) is connected to enclosure or housing 30 via a plurality of vacuum ports 42, with a port being located in each of the three housing compartments or chambers 44, 46 and 48, as described in greater detail hereinafter. Rotatably supported in housing chamber 46 is a pair of moving belt idler pulleys 40, such being secured by means not shown to a wall of housing 30. Chambers 44 and 46 are separated by a baffle plate or wall 50 having a pair of small slits therein, while chambers 46 and 48 are separated by a baffle plate 52 having a pair of slits therein. The slits in plates 50 and 52 are offset from one another as described in greater detail hereinafter, and provide for passage of moving belt 54 through plates 50 and 52. Each of the chambers 44, 46 and 48 are provided with windows, not shown, through which the operation of the moving belt may be observed. While not shown, chambers 44, 46 and 48 are connected to a three stage stand-alone (portable) vacuum station to provide pressure differentials between the chambers by differential pumping.

Attached at one end of housing 30 is a flange or collar 56 having an opening 57 which is aligned with opening 31 in housing 30, flange 56 supporting one (inner) end of a hollow member or tube 58 which forms an outer casing of probe 17 of FIG. 1. The opposite (outer) end of the probe casing or tube 58 is supported in and secured to mass spectrometer 14 by a vacuum interface, generally indicated at 60. The vacuum interface 60 includes a coupler, generally indicated at 60', and a seal 61, such as an O-ring, so as to secure tube 58 to mass spectrometer 14 in a vacuum tight arrangement. The coupler 60' includes a member secured to mass spectrometer 14 and a member positioned around tube 58 and which are interconnected by threads, such that the seal 61 is tightly held between the coupler members to provide a vacuum tight interconnection or interface.

Figure 4:
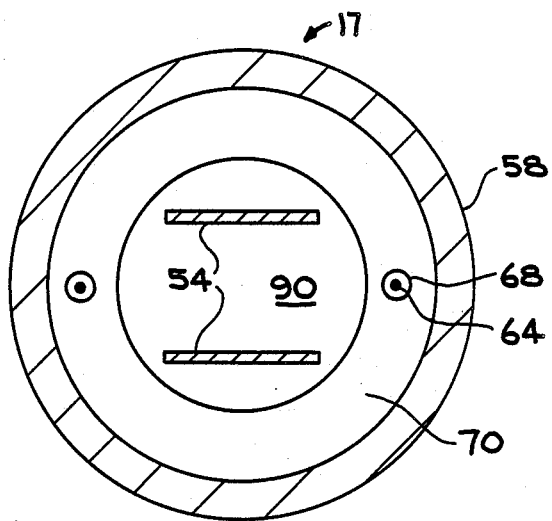
FIG. 4 is an enlarged, cross-sectional view of the heating circuitry of the probe relative to the moving belt of the interface of FIG. 2.
Figure 3:
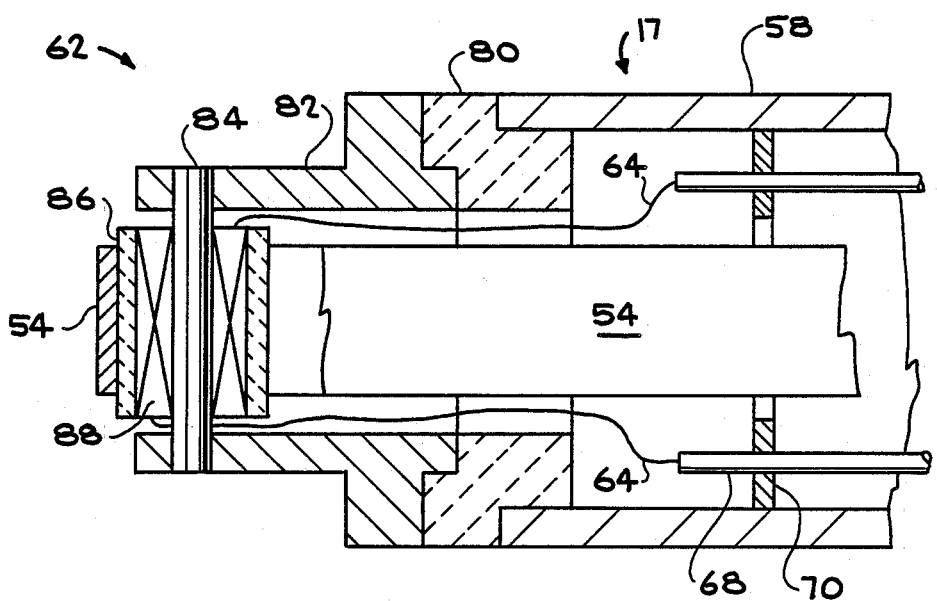
FIG. 3 is an enlarged, partial cross-sectional view of the moving belt tip of the interface of FIG. 2.

Attached at the inner end of probe casing or tube 58 and extending outwardly therefrom is a heated probe tip, generally indicated at 62, around which the moving belt 54 passes. The detailed construction of the probe 17 and heated probe tip 62 is illustrated in FIGS. 3 and 4 and is described in detail further on in this description. Electrical leads or wires indicated at 64 extend from heater and temperature control 20 (see FIG. 1) through an insulative feed thru seal 66 mounted in chamber 48 of housing 30 through small tubes or conduits 68 to heated probe tip 62. A pair of spaced washer-like members 70 form supports for tubes 68, members 70 being constructed such that moving belt 54 passes therethrough. The heated probe tip 62 extends into and is located within chamber 72 of mass spectrometer 14 formed by walls 74 (only one shown through which probe 62 extends), and causes the chemical residue on moving belt 54 to neat up and ionize or sublime off into the ion source of mass spectrometer 14, as indicated at 76.

Optionally, the residue on belt 54 may be directly ionized by directing an electron or fast atom or photon beam, indicated at 78, from an externally located fast atom bombardment (FAB) gun, or an electron or photon gun, shown in block diagram form in FIG. 2, onto the residue at the end of the moving belt. Direct ionization by fast atom bombardment using FAB guns is known in the art and need not be described in detail here. Such a direct ionization approach is described in the reference, R. D. Smith et al., Anal. Chem., 53, 1603–1611 (1981), cited earlier in the background section. While not shown, a detector mechanism may also be attached in or to the wall 74 of mass spectrometer 14, adjacent heated probe tip, to provide for the detection and identification of the ionized species and thereby to determine the efficiency of the improved moving belt interface of the present invention.

Referring now to FIGS. 3 and 4, the probe 17 and heated probe tip 62 are illustrated in greater detail. The probe tip 62 includes a hollow tip insulator 80, constructed of ceramic or glass or other suitable inert insulative materials, for example, is secured in the end of casing or tube 58, constructed of a material such as aluminum or stainless steel or any other inert material which would maintain the integrity of the vacuum system, with a hollow support member or collar 82, secured to insulator 80, and constructed of a material such as aluminum or stainless steel or any other inert material which would maintain the integrity of the vacuum system. Mounted in support member 82 is a roller axle or shaft 84 on which is mounted a ceramic roller 86, the axle 84 being constructed of a material such as aluminum or stainless steel or any other inert material which would maintain the integrity of the vacuum system. Roller 86 may be constructed of any other suitable, inert, insulative material. Mounted in roller 86 is a heater/temperature sensor assembly 88 which is operationally connected to electrical wires or leads 64. The tension on the moving belt 54 keeps the components of the heated probe tip in place. However, these components may be bonded or otherwise secured together but such that roller 86 is allowed to rotate freely on axle 84. In one embodiment, the heater/temperature sensor assembly 88 is constructed so as to rotate with roller 86 while the electrical leads 64 remain in a fixed position, while in another embodiment, the heater/temperature sensor assembly 88 is constructed so as not to rotate within roller 86 while the electrical leads 64 remain in a fixed position. The leads or wires 64 extend through a pair of spaced support tubes or conduits 68 which in turn are supported by hollow members or washers 70 which include a central opening 90 through which moving belt 54 passes, as shown in FIG. 4. By way of example, the wires 64 may be constructed of tungsten or copper, the tubes 68 constructed of any suitable, inert material such as plastic or nylon and the hollow support members 70 constructed of any suitable, inert material such as aluminum, stainless steel and the like. The moving belt 54 is constructed of any suitable inert materials which are flexible, strong and capable of withstanding nigh temperatures and corrosive or organic solvents typically employed in HPLC, as well as chemical reactions due to the direct ionization of the chemical residue thereon by fast atom bombardment. Exemplary materials include but are not limited to Kapton, nylon, mylar or stainless steel, more preferably, stainless steel, having a width of about 40 mils to about 50 mils, thickness of about 2 to about 5 mils, and typically a length of about 30 inches to about 40 inches.

Figure 5:
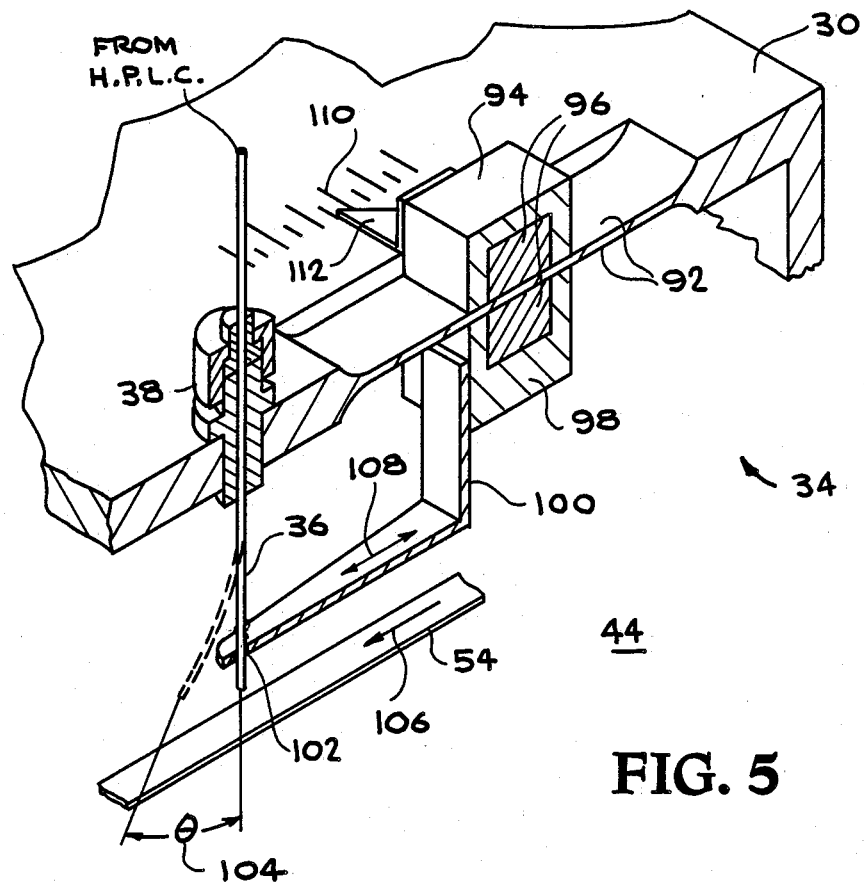
FIG. 5 illustrates the remotely controlled, magnetically coupled system for adjusting the angle of the deposition of the HPLC effluent onto the moving belt of the FIG. 2 interface.

FIG. 5 snows the remote magnetic slide system 34 for positioning or adjusting the capillary or HPLC effluent tube 36 without affecting the vacuum integrity of the interface. The angle between the moving belt 54 and the position of the nozzle or tip of tube 36 is critical for proper deposition of a thin, uniform layer of the HPLC effluent on the belt, effluents carrying different materials requiring different angles. Housing 30 is provided with a reduced thickness section forming a slot or track 92 on the outer side of which is located a master block 94 within which is a magnet 96, and on the inner side is located a slave block 98 within which is another magnet 96. Secured to slave block 98 is an L-shaped tube support or bracket 100 having an opening 102 in the end thereof through which tube 36 extends. An angle $\theta$, indicated at 104, at which the HPLC effluent contacts the belt 54, and the quantity of the effluent contacting the belt 54, is dependent on the speed and direction of travel of the belt, indicated at 106, and the position of the bracket 100, movement of the bracket 100 being indicated at 108. Thus, the movement of bracket 100 to the left, as shown, increases the angle $\theta$ while movement to the right decreases $\theta$. A scale 110 is located on the outer surface of housing 30 and a pointer or indicator 112 is secured to master block 94. The magnets 96, for example, may be of the cobalt-samarium type and the system 34 is constructed such that sliding the master block 94 along track 92 to the selected place or position on scale 110, causes a similar or identical movement of slave block 98 due to the coupling of magnets 96, which causes movement of bracket 100 which, in turn, changes the location of the nozzle or tip of tube 36 relative to or according to scale 110, thereby changing angle $\theta$. Thus, the deposition of the HPLC effluent onto the moving belt 54 is remotely controlled, and without any additional openings (with the associated vacuum leak problems) being provided in housing 30.

Figure 6:
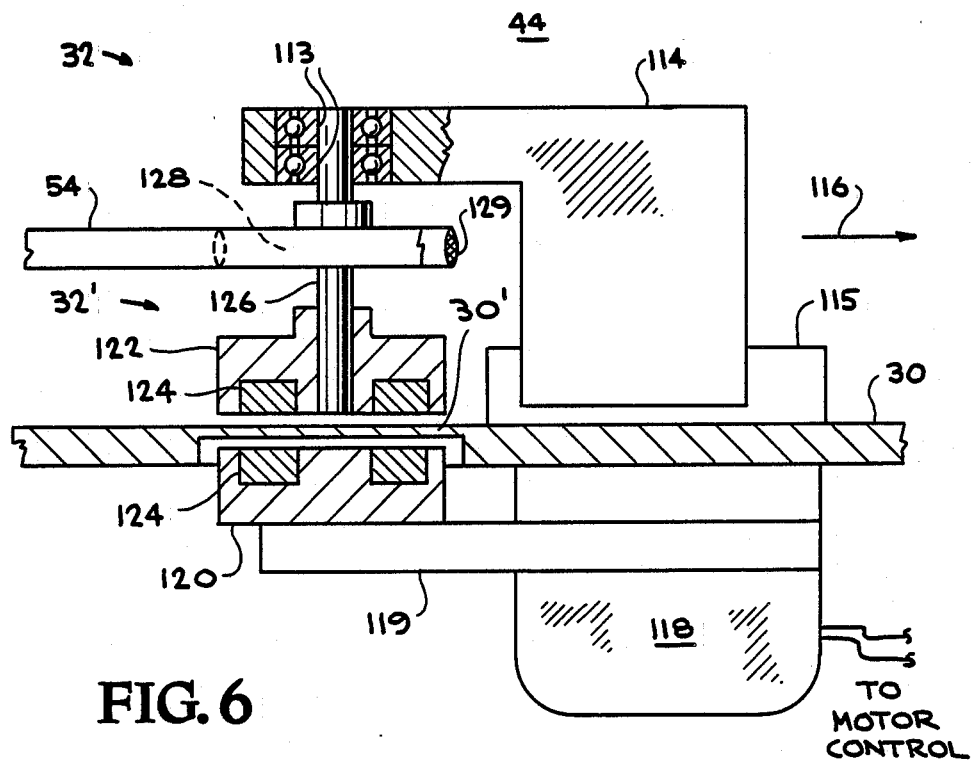
FIG. 6 illustrates an embodiment of the magnetically coupled, remote drive system for the belt of the FIG. 2 interface.

The remote magnetic drive system 32 for moving belt 54 is shown in FIG. 6, which includes an internally located belt tensioning device 114, of the spring type, not shown, which is moved by the spring force as indicated by arrow 116 to apply tension to or adjust the tension of belt 54. Spring tensioning mechanisms are known in the art and a detailed description thereof is deemed unnecessary. To increase the tension on belt 54, the belt tensioning device is moved to the right, direction of arrow 116, with respect to a support member 115 secured to an inner surface of housing 30.

As shown in FIG. 6, the drive system 32 o includes an electric drive motor 118 which is connected electrically to motor contact 22 (see FIG. 1) via leads, as indicated by legend. The drive system 32 includes an unique magnetically coupled drive-train mechanism, generally indicated at 32', which smoothly turns moving belt 54 with great force and includes a main drive-train, non-slip pulley over which the moving belt travels. The pulley includes a curved surface that continuously centers the belt. The drive-train mechanism 32' is coupled to drive motor 118 by a coupling 119, which may be of a belt, chain or gear type. The mechanism 32' includes a drive block 120, a driven block 122, a plurality of magnets 124 located within blocks 120 and 122 (although a pair may be sufficient), a shaft 126 secured at one end to driven block, a drive pulley 128 secured to shaft 126 and over which belt 54 passes, and a ball bearing assembly 113 mounted in belt tensioning device 114 which supports the opposite end of shaft 126. The drive block 120 is located in a counter-sink in housing 30 which defines a thin wall section 30', with the blocks 120 and 122 located on opposite sides of wall section 30' and retained in alignment by magnets 124. The magnets 124 are, for convenience, of the cobalt-samarium type which magnetically couple the drive and driven blocks such that movement of drive block 120 via drive motor 118 and coupling 119 causes simultaneous movement of driven block 122 and rotation of shaft 126 and drive pulley 128. Drive motor 118, as controlled by motor control 22 may be driven in the forward or reverse directions and at variable speed, thereby controlling the likewise movement of the belt 54 in the forward, reverse directions and at variable speed. Note that the countersink area of wall 30 is larger than the cross-section of driven block 120 so as to allow for the movement of drive block 120 on account of the movement of belt tensioning device 114 in a direction indicated by arrow 116 for example, which causes corresponding movement of shaft 126, drive pulley 128 and driven block 122. Thus the drive and driven blocks 120 and 122 maintain their aligned relationship due to the strength of the magnets 124. The drive-train mechanism 32', therefore, does not require the drilling of any holes in housing 30 which could compromise the integrity of the vacuum system of the interface. The outer surface or periphery of pulley 128 is provided with a concave or slightly curved surface which is lined or coated with a plastic material indicated at 129, having a convex outer surface that functions to continuously center the belt 54. The main pulley 128, preferably constructed out of aluminum or stainless steel, is also provided, by the plastic material 129, with a non-slip outer surface, this being done by infusing a plastic type material into the stainless steel or aluminum surface.

Figures 7, 8:
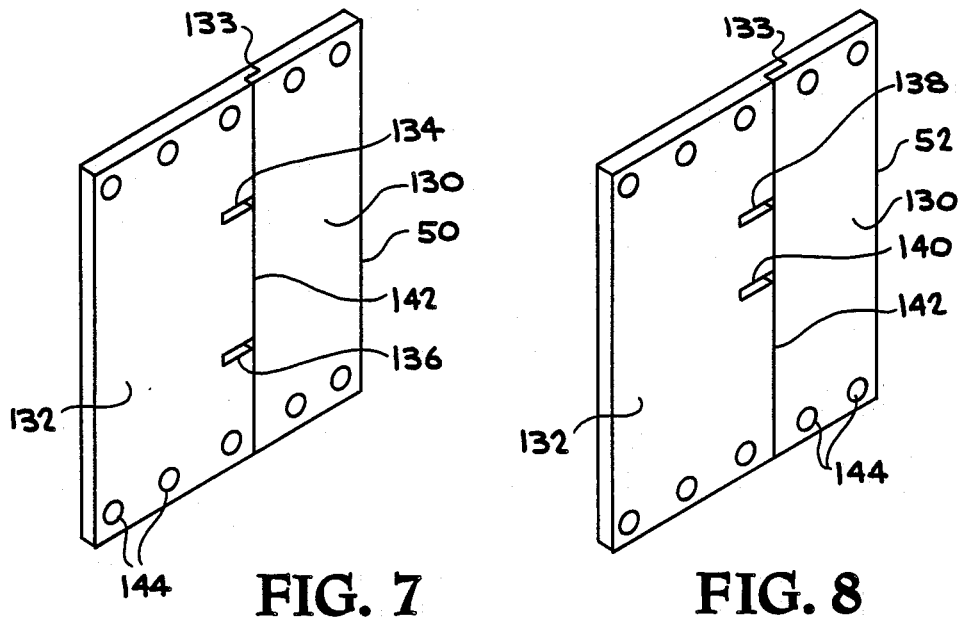
FIGS. 7 and 8 are enlarged views which show embodiments of baffle plates within the interface of FIG. 2, which separate the vacuum stations (allowing for differential pumping) while allowing passage of the moving belt through offset openings or slits in the plates.

To ensure vacuum integrity between chambers 44, 46 and 48 of housing 30, baffle plates 50 and 52, which separate the chambers, are constructed as shown in FIGS. 7 and 8. Each of the baffle plates 50 and 52 are constructed in two sections 130 and 132 which are interconnected by a step structure 133. Plate 50 is provided with a pair of spaced slits or slots 134 and 136, while plate 52 is provided with a pair of slits or slots 138 and 140. Note that each of the slits is formed in one of the two sections of the plates adjacent a split 142 therebetween, to provide for the dove-tailing of the two sections and for ease of forming the slits. It is also to be noted that the slits in plate 50 are not in exact alignment with the slits in plate 52, which enables better vacuum integrity. Note, however, the upper slits or slots 134 and 138 (as shown in FIG. 2) appear to be nearly axially aligned but are in actual practice slightly offset from each other. The slits or slots in plates 50 and 52 are constructed so as to allow for passage of moving belt 54 therethrough without the belt rubbing on the edges of the slits, which would cause wear, and in the case of the upper and outer side of belt 54, could result in partial removal or loss of the chemical residue carried on and by the belt. Plates 50 and 52 are provided with holes 144 along the upper and lower edges for alignment and mounting of the plates within housing 30. while not shown, the plates may be secured to the inner walls of housing 30 by small L-shaped connectors secured in holes 144 and secured to the adjacent housing wall. However, other securing means for the plates may be utilized. As shown in FIG. 2, idler pulleys 40 function to direct movement of belt 54 from slit or slot 140 in baffle plate 52 to slit or slot 136 in baffle plate 50. Because of the possibility that sample material (residue) being carried on the belt's upper surface might be rubbed off during transport, care must be taken to maintain the maximum offset between slits or slots 138 and 134 so that there is no friction or rubbing of the upper surface of the belt 54 on the plates 50 or 52 as the belt 54 passes through these slots.

By way of example, if the HPLC effluent carries a polar or biological compound, the angle $\theta$ of tube 36 would be about 26°, with the pressure in chambers 44, 46 and 48 being about $10^{-3}$, $10^{-4}$, and $10^{-5}$ Torr respectively. The exemplary speed of movement of belt 54 would be about 100 cm per minute, and the temperature at the heated probe tip 62 would be about 300° C. while preferred but not essential, each of the components located within the three chambers of housing 30, particularly components in chamber 44, and within tube 58 of probe 17 should be constructed of material resistant to corrosive and organic solvents from the HPLC effluent.

It has thus been shown that the improved moving belt interface of this invention provides a rugged, portable HPLC-MS interface that possesses the desirable attributes of other types of interfaces discussed above, yet is relatively simple in construction and inexpensive, while being adaptable to all types and makes of mass spectrometers, with minor, if any, modification of the existing mass spectrometer. In addition, the interface of this invention is particularly adapted for analyses of polar compounds which hithertofore have been very difficult because these compounds decompose with neat or are so highly polar that they interact with the solvents or other components and cannot be readily volatalized directly into the ion source of the mass spectrometer. Furthermore, this invention provides an HPLC-MS interface which utilizes a heated probe tip to rapidly heat and sublime off the chemicals on the moving belt and/or to ionize the chemicals off by electron, photon or fast atom bombardment using a FAB, electron or photon gun or any other ionizing means that is located external to the interface. Thus, the HPLC-MS interface of this invention has substantially advanced the state of the art of moving belt interfaces, particularly in view of the magnetically coupled drive system, differentially pumped sections, portability and the calibrated control system for the nozzle for discharge of the HPLC effluent.

While the moving belt interface of this invention has been described as HPLC-MS interface, the effluent directed onto the moving belt may be supplied by means other than an HPLC column, and it is not intended to limit the invention to use only with an HPLC column and/or a mass spectrometer.

While a particular embodiment of the invention and specific materials and parameters have been illustrated and described, the invention is not limited to the particular illustrations or embodiments so described. The above embodiments were chosen and described in order to explain best the principles and the practical application of the subject invention thereby to enable those skilled in the art to utilize the invention in various other embodiments and various modifications as are suitable for the particular use contemplated. The foregoing description of preferred embodiments of the invention have been presented therefor for purposes of illustration and description. It is not intended to be exhaustive or to limit the invention to the precise form disclosed, and obviously many modifications and variations are possible in light of the above teaching. It is intended that the scope of the invention be defined by the claims appended hereto.

What is claimed is:

1. A moving belt interface comprising:
a vacuum tight housing having a plurality of chambers therein, each of said chambers being constructed and arranged to be connected to a vacuum pumping means, said housing being provided with at least one opening:
a probe assembly operatively connected to said housing and in alignment with said opening, said probe assembly including a tip section which includes a rotatable member and means for heating said rotatable member;
a continuous belt positioned in said housing and said probe assembly so as to extend into each of said plurality of chambers in said housing and around said rotatable member of said probe assembly tip section, said belt being constructed of material which is substantially nonstretchable and chemically nonreactive to material positioned thereon and which is nonreactive to fast atom bombardment;
means for rotating said continuous belt;
means for directing material onto said belt; and
means for selectively controlling an angle at which material is directed from said material directing means onto said belt, such that material is deposited on said belt in a thin, uniform layer.

2. The moving belt interface of claim 1, wherein said means for rotating said continuous belt includes a pulley around which said belt passes, said pulley being located within a first of said plurality of chambers of said housing, a driving means located externally of said housing, and magnetic coupling means interconnecting said driving means with said pulley.

3. The moving belt interface of claim 2, wherein said magnetic coupling means includes a driver block located externally on said housing and operationally connected to said driving means,
a driven block located within said first chamber of said housing and aligned with said driver block,
magnet means located within each of said driver and driven blocks, and a shaft connecting said driven block to said pulley.

4. The moving belt interface of claim 3, additionally including belt tensioning means located within said first chamber, wherein said belt tensioning means includes a spring force-activated mechanism operatively connected to said pulley via said shaft of said magnetic coupling means.

5. The moving belt interface of claim 3, additionally including means for controlling said driving means.

6. The moving belt interface of claim 3, wherein said pulley includes means for providing a non-slip outer surface and for maintaining said belt centrally thereon.

7. The moving belt interface of claim 1, wherein said means for directing material onto said belt includes a flexible tube partially located in a first chamber of said plurality of chambers of said housing, and wherein said angle controlling means includes a magnetically coupled mechanism operatively connected to said flexible tube, whereby movement of said magnetically coupled mechanism moves said flexible tube and changes the angle at which material from said flexible tube is directed onto said belt.

8. The moving belt interface of claim 7, wherein said magnetically coupled mechanism includes a first magnetic member located externally of said housing adjacent said first chamber, a second magnetic member located internally in said first chamber of said housing and in alignment with said first magnetic member, means interconnecting said second magnetic member with said flexible tube, such that movement of said first magnetic member causes corresponding movement of said second magnetic member and movement of said flexible tube with respect to said belt thereby changing said angle.

9. The moving belt interface of claim 8, wherein said magnetically coupled mechanism also includes an indicator secured to said first magnetic member, and a scale secured to an external surface of said housing, said indicator being constructed and arranged to be moved along said scale by movement of said first magnetic member, said scale being calibrated to correspond to angles between said belt and said flexible tube.

10. The moving belt interface of claim 1, wherein a pair of said plurality of chambers of said vacuum tight housing are separated from each other by at least one plate positioned in and secured to said housing, said at least one plate being provided with a pair of slits therethrough through which said continuous belt passes, said slits being constructed to maintain vacuum integrity in each of said chambers.

11. The moving belt interface of claim 10, wherein said vacuum tight housing contains three chambers, said three chambers being separated by a pair of said plates, said pair of slits in a first of said pair of plates being axially offset from said pair of slits in a second of said pair of plates so that said slits are not in exact alignment with one another.

12. The moving belt interface of claim 10, additionally including a pair of idler members located in a second of said plurality of vacuum chambers of said housing, said idler members being located on opposite sides of said continuous belt and positioned to change direction of a path of travel of said belt between said probe assembly tip section and said means for rotating said continuous belt.

13. The moving belt interface of claim 1, wherein said probe assembly additionally includes an outer hollow casing having one end secured to said housing and in alignment with said opening in said housing, said tip section being mounted to an opposite end of said hollow casing, and said means for heating said rotatable member being operatively connected to a control mechanism located externally of said housing and of said probe.

14. The moving belt interface of claim 13, wherein said rotatable member of probe tip section is rotatably mounted in a member connected to said opposite end of said hollow casing via an insulator member, and wherein said means for heating said rotatable member is located within said rotatable member.

15. The moving belt interface of claim 13, wherein said means for heating said rotatable member constitutes an electrical heating mechanism which is operationally connected to said control mechanism by a pair of electrical leads, each of said pair of electrical leads extending from said control mechanism through an insulative seal in said housing, and through a tube which extends longitudinally within said hollow casing, to said means for heating, each tube through which an electrical lead extends being supported within said hollow casing, said hollow casing being constructed so that said continuous belt passes therethrough in spaced relation with said longitudinally extending tubes for said pair of electrical leads.

16. The moving belt interface of claim 1, additionally including a multiple stage, stand-alone vacuum pump mechanism operationally connected to each of said plurality of chambers of said housing.

17. The moving belt interface of claim 1, in combination with a mass spectrometer and a high performance liquid chromatography column, said probe tip section of said moving belt interface being positioned in vacuum sealed relation within said mass spectrometer, said means for directing material onto said belt being operationally connected to said high performance liquid chromatography column, whereby at least a portion of material directed onto said belt is carried by said belt into said mass spectrometer, wherein such material is heated and sublimed off said belt by said means for heating said rotatable member located within said probe tip section.

18. The combination of claim 17, additionally including means for ionizing material carried by said belt, positioned to direct an ionizing beam onto said probe tip section for direct ionization of material on said belt.

19. The combination of claim 17, additionally including a coupling and seal means for mounting said moving belt interface to said mass spectrometer in the vacuum sealed relation.

20. The moving belt interface of claim 1, wherein said angle is about 26°.

21. In a mass spectrometer-liquid chromatography system having a moving belt interface therebetween, the improvement wherein the interface comprises:
a vacuum tight housing having three chambers therein, each of said chambers being adapted to be connected to a vacuum pumping means, constructed and arranged to produce different pressures in each of the chambers, said housing being provided with at least one opening;
a probe assembly operationally connected to said housing and in alignment with said opening, said probe assembly including a tip section which includes a rotatable member and means for heating said rotatable member, said tip section of said probe assembly being adapted to be inserted into an associated mass spectrometer;
a continuous belt constructed of stainless steel positioned in said housing and said probe assembly so as to extend into each of said three chambers of said housing and around said rotatable member of said probe assembly tip section;
means including a magnetically coupled drive-train for rotating said continuous belt;
means including a magnetic coupling for selectively controlling an angle at which material is directed from said material directing means onto said belt in a thin, uniform layer.

22. The improvement of claim 21, wherein said angle is about 26°.

* * * * *